(12) United States Patent
Yamauchi

(10) Patent No.: US 7,484,401 B2
(45) Date of Patent: Feb. 3, 2009

(54) GAS SENSOR

(75) Inventor: Masanobu Yamauchi, Kariya (JP)

(73) Assignee: Denso Corporation (JP)

( * ) Notice: Subject to any disclaimer, the term of this patent is extended or adjusted under 35 U.S.C. 154(b) by 235 days.

(21) Appl. No.: 11/592,247

(22) Filed: Nov. 3, 2006

(65) Prior Publication Data

US 2007/0101801 A1    May 10, 2007

(30) Foreign Application Priority Data

| Nov. 4, 2005 | (JP) | ............................. 2005-321156 |
| Jun. 30, 2006 | (JP) | ............................. 2006-181907 |

(51) Int. Cl.
*G01N 7/06* (2006.01)
(52) U.S. Cl. .................................... 73/23.32
(58) Field of Classification Search ............... 73/23.32, 73/23.31; 204/424
See application file for complete search history.

(56) References Cited

U.S. PATENT DOCUMENTS

| 4,717,464 | A | * | 1/1988 | Oshima et al. ............... 204/427 |
| 4,765,881 | A | * | 8/1988 | Wertheimer et al. ......... 204/428 |
| 5,874,664 | A | * | 2/1999 | Watanabe et al. ........... 73/23.32 |
| 6,178,806 | B1 | * | 1/2001 | Watanabe et al. ........... 73/23.32 |
| 6,296,748 | B1 | * | 10/2001 | Ohtsuki et al. ............... 204/427 |
| 6,817,224 | B2 | * | 11/2004 | Hibino et al. ............... 73/23.31 |

FOREIGN PATENT DOCUMENTS

| JP | 11-248671 |   | 9/1999 |
| JP | 2001215210 | A  * | 8/2001 |
| JP | 2001242118 | A  * | 9/2001 |

* cited by examiner

*Primary Examiner*—John Fitzgerald
(74) *Attorney, Agent, or Firm*—Nixon & Vanderhye PC

(57) ABSTRACT

A gas sensor having an elastic insulating member including a longitudinal hole for receiving an air permeability filter assembly and a passage portion communications between the longitudinal hole and an outer side thereof.

20 Claims, 13 Drawing Sheets

GAS SENSOR

CROSS REFERENCE TO RELATED APPLICATION

This application is based on Japanese Patent Application No. 2005-321156 filed on Nov. 4, 2005, and Japanese Patent Application No. 2006-181907 filed on Jun. 30, 2006 the disclosure of which is incorporated herein by reference.

FIELD OF THE INVENTION

The present invention relates generally to a gas sensor which may be installed in an exhaust system for measuring a particular gas content in a measurement gas.

BACKGROUND OF THE INVENTION

Japanese Patent Laid-open Publication No. 1999-248671, describes a gas sensor that may be employed in an oxygen measuring device of an air-fuel ratio control system. The gas sensor measures an oxygen content in exhaust gasses of an internal combustion engine of an automotive vehicle and so on.

As shown in FIG. 20, a gas sensor 9 holds therein a sensor element 910 that detects a concentration of a particular gas in a measurement gas. A housing 911 holds therein a sensor element 910 via an insulation porcelain 913. An air cover 92 is installed on the base portion of the housing 911.

An elastic insulating member 93 is installed in the base portion of the air cover 92. The elastic insulating member 93 receives lead wires 912 that make an electric contact at one end with the sensor element 910.

An outer cover 94 is installed on the base portion of the air cover 92. The outer cover 94 is calked in a radially inner direction at three axially spaced calking portions 940.

Furthermore, an air permeability filter 95 having a waterproof property is held between the air cover 92 and the outer cover 94 and crimped to be retained by two of the calking portions 940. Air as a reference gas is introduced from a through hole 941 in the outer cover 94 to an air vent 921 of the air cover 92 via the air permeability filter 95. After that the air is introduced into gas sensor 9.

In this conventional gas sensor 9, however, since the air permeability filter 95 is retained between the air cover 92 and the outer cover 94, the air permeability filter 95 easily receives heat via the air cover 92 or the outer cover 94. Therefore, when the gas sensor 9 is used in a exhaust of the internal combustion engine any number of times, the permeability filter 95 is subject to heat deterioration and the waterproof property at the calking portions 940 that retain the permeability filter 95 may fail. Thus, there is the concern that outside water will infiltrate into the gas sensor 9 through the air vent 921.

SUMMARY OF THE INVENTION

In view of the above-described problems, it is an object of the present invention to provide an improved gas sensor structure which provides an air permeability portion that can maintain its waterproof property.

According to an aspect of the invention, there is provided a gas sensor which features an air permeability portion. The gas sensor comprises; a sensor element detecting the concentration of the particular gas contained in the measurement gas; a housing holding said sensor element; an air cover installed on an end of said housing; a lead wire making an electric contact with said sensor element; an elastic insulating member having a lead wire insertion hole for receiving said lead wire and sealing the base portion of said air cover; wherein said elastic insulating member has a longitudinal hole, formed in the axial direction thereof and open at an end thereof, a passage portion communicating between said longitudinal hole and an outer side thereof; a tubular member forming an internal space that is open at an end thereof and having a through-hole penetrating between said internal space and an outer side of said tubular member is disposed in said longitudinal hole; an air permeability filter wound around an outer circumference of said tubular member and crimped between said elastic insulating member and said tubular member; said air cover is a radially calked at plural axially spaced calking portions to retain said elastic insulating member, and an air vent, through which air is admitted into said passage portion of said elastic insulating member is disposed between said multiple calking portions.

BRIEF DESCRIPTION OF THE DRAWINGS

Other objects, features and advantages of the present invention will become more apparent from the following detailed description made with reference to the accompanying drawings, in which.

DETAILED DESCRIPTION OF THE PREFERRED EMBODIMENTS

In this application, the installed side in an exhaust pipe of an internal combustion engine for a wide variety of vehicles is defined as the top end side and the opposite end is defined as the base end side.

EXAMPLE 1

Figure 1:
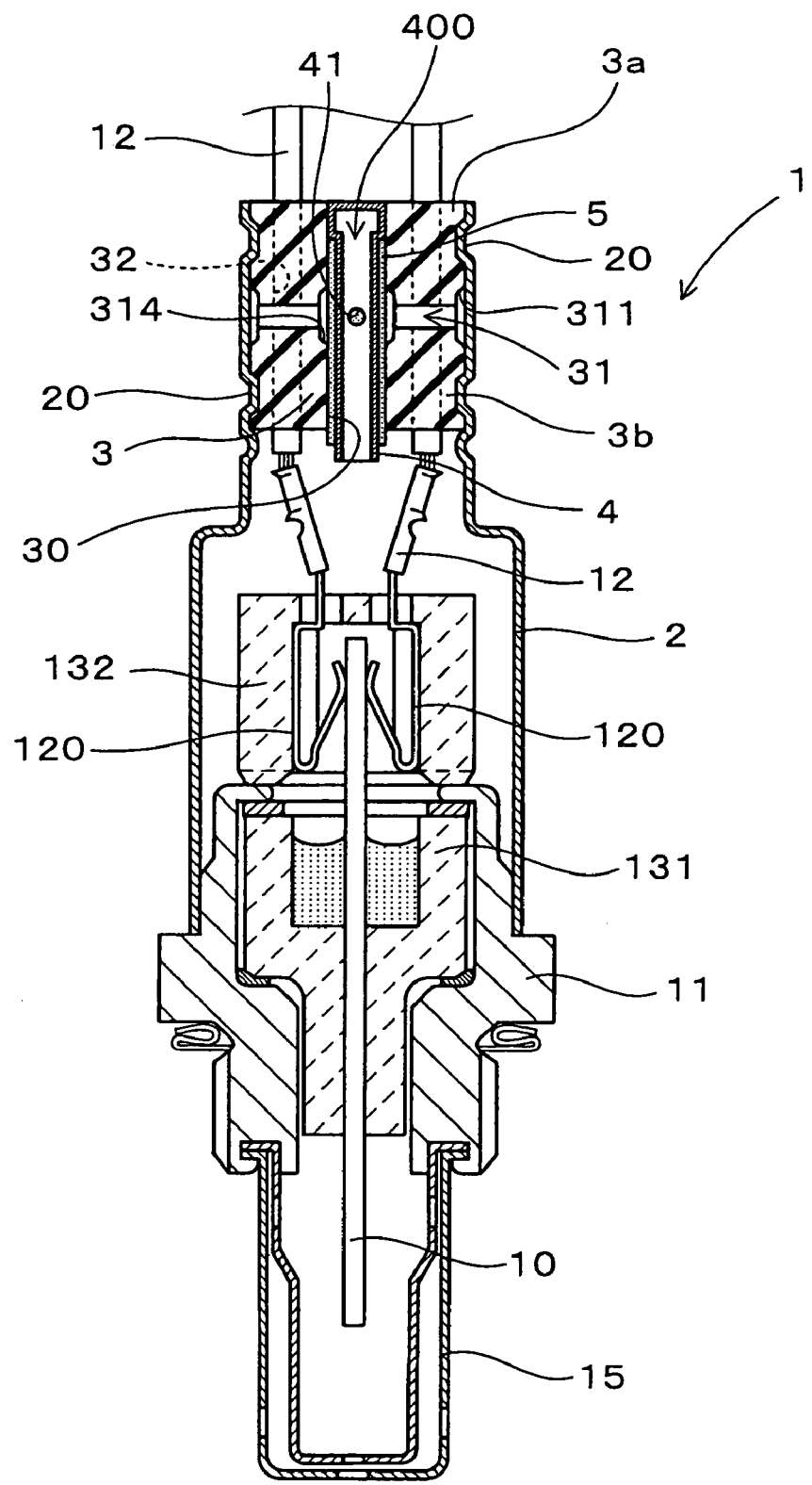
FIG. 1 is a longitudinal sectional view which shows a gas sensor according to a first example embodiment of the present invention.

Referring to the drawing, wherein like reference number refer to like parts in several views, particularly to FIG. 1, there is shown a gas sensor 1 according to a first example embodiment of this invention.

The gas sensor includes a sensor element 10 that detects the concentration of a particular gas included in the measurement gas, a housing 11 that receives the sensor element 10, an air cover 2 that is fitted on the base portion of the housing 11, lead wires 12 that make an electric contact with the sensor element 10, an elastic insulating member 3 that passes the lead wires 12 and that seal the base portion of the air cover 2.

As shown in FIGS. 1-5, the elastic insulating member 3 has a longitudinal hole 30 formed in the axial direction thereof and opened at the top end portion, a passage portion 31 communicating with the longitudinal hole 30, and four lead wire insertion holes 32 receiving four lead wires 12.

Figure 7:
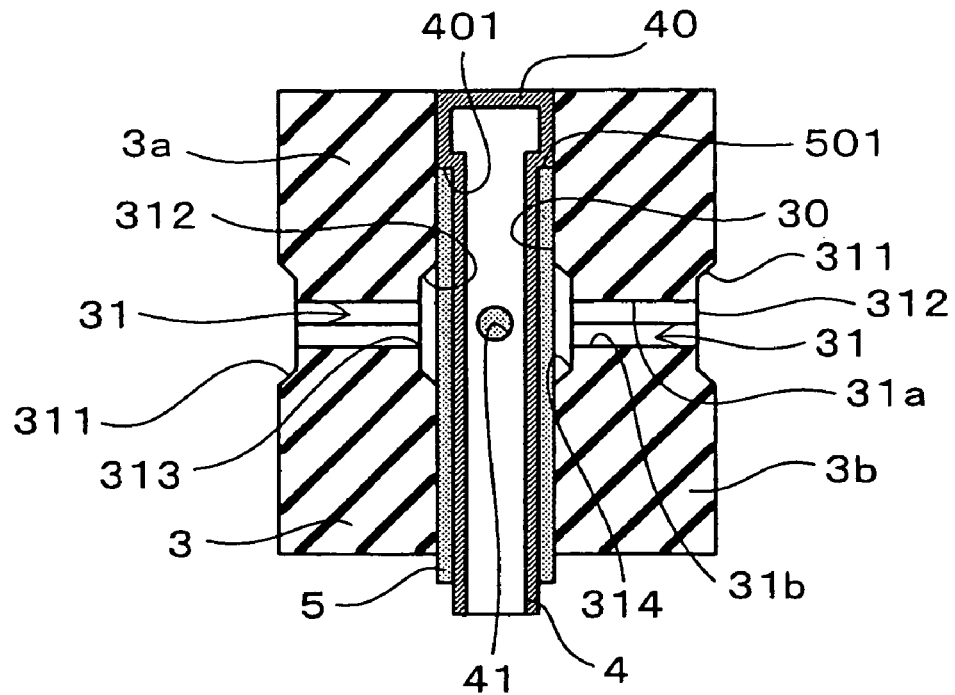
FIG. 7 is a longitudinal sectional view which shows the assembled elastic insulating member, tubular member, and air permeability filter of the gas sensor according to the first example embodiment of the present invention.
Figure 8:
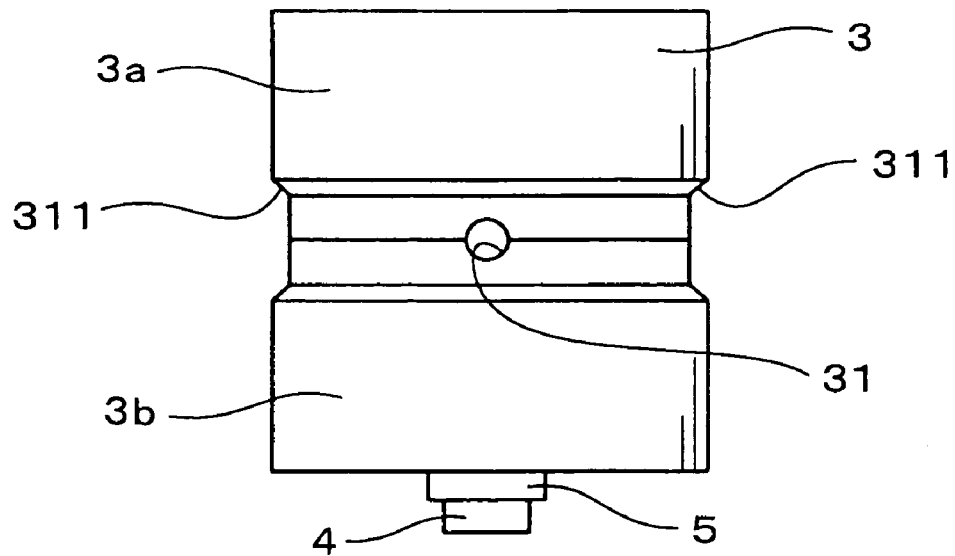
FIG. 8 is a side view which shows the assembled elastic insulating member, tubular member, and air permeability filter of the gas sensor according to the first example embodiment of the present invention.

As shown in FIGS. 1-8, a tubular member 4 having two through holes 41 passing between an inner space 400 thereof and an outer side face is disposed in longitudinal hole 30. A tubular shaped air permeability filter 5 is wound around an outer circumference of the tubular member 4 to be inserted between the tubular member 4 and the longitudinal hole 30. As shown in FIG. 8, the air permeability filter 5 is clamped to be held between the elastic insulating member 3 and the tubular member 4.

As an example, the air permeability filter 5 has an air permeability property and is made of porous polytetrafluoroethylene (PTFE).

The air permeability filter 5 can be superior in waterproof property, heat resistance and chemical resistance to maintain air introduction.

Figure 2:
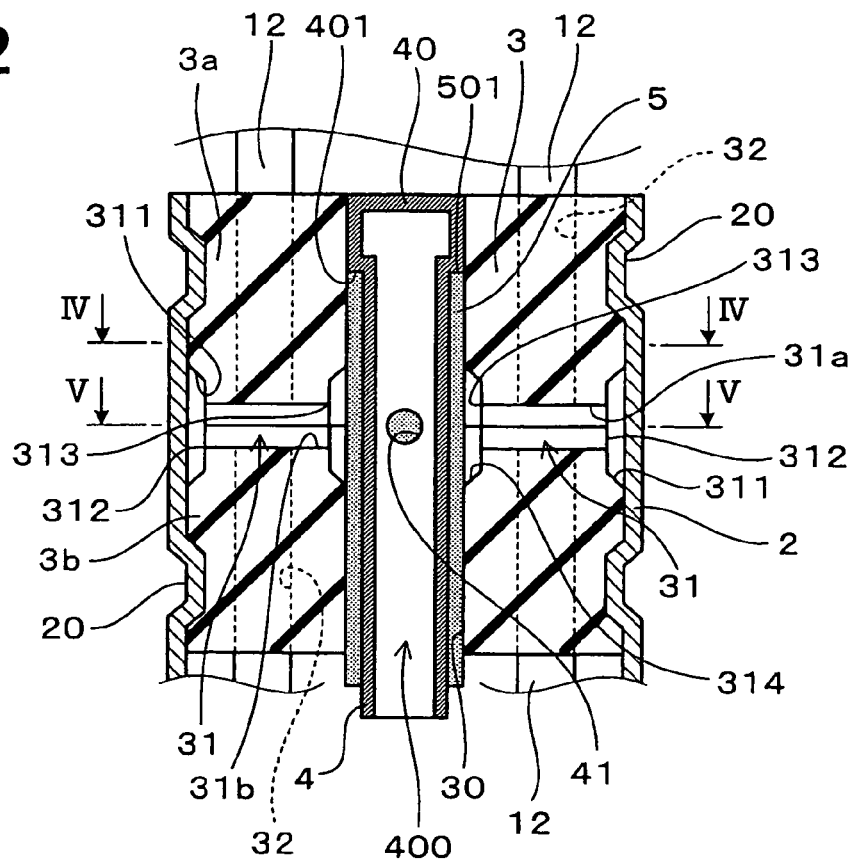
FIG. 2 is a longitudinal sectional view which shows an base portion of the gas sensor of FIG. 1.
Figure 3:
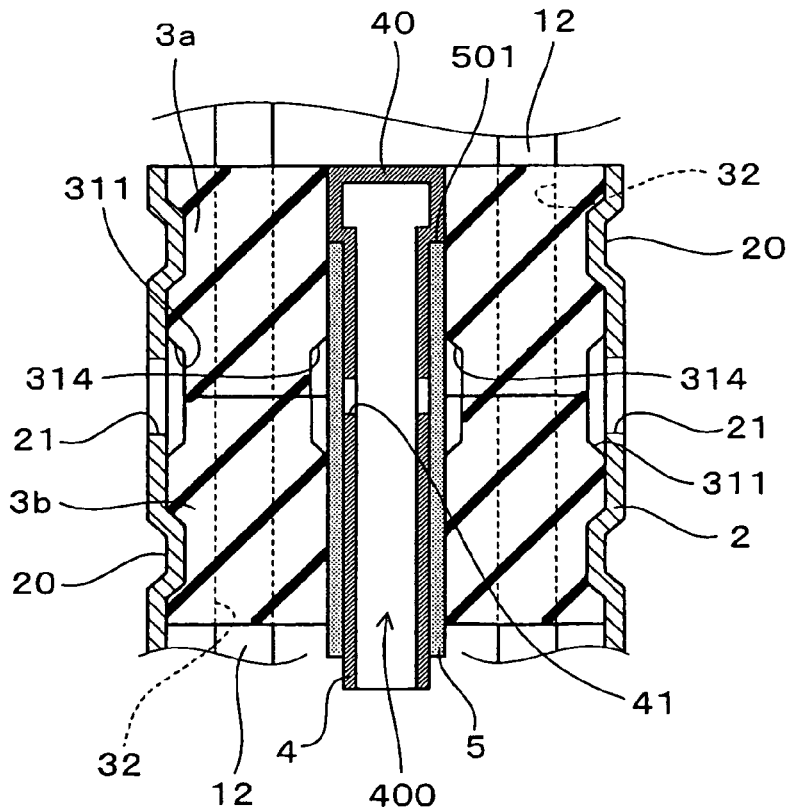
FIG. 3 is a longitudinal sectional view which shows the base portion of the gas sensor in the cross-direction of FIG. 2.

As shown in FIGS. 1-3, the air cover 2 has two axially spaced calking portions 20 where it is radially calked to the elastic insulating member 3. Two air vents 21 are formed between the calking positions. The two air vents 21 communicate with the two passage portions 31 of the elastic insulation member 3.

Although two air vents and two passage portions are illustrated in this example, more or fewer vents and passages can be provided and the member of vents does not have correspond with the number of passages.

As shown in FIG. 1, the first insulation porcelain 131 is held in the housing 11 and the second insulation porcelain 132 is disposed on the base side of the housing 11.

The sensor element 10 is inserted to be retained by the first insulation porcelain 131 and the base portion of the sensor element 10 is surrounded by the second insulation porcelain 132. On the other hand, an element cover 15, which protects the top portion of the sensor element 10, is installed at the top portion of the housing 11.

The sensor element 10 is made of a detecting portion for detecting the concentration of the particular gas, a heater for heating the detecting portion, and terminals making electric contact with the detecting portion and with the heater (not shown).

The terminals are connected with four lead wires 12 through connecting terminals 120. The connecting terminals 120 are disposed in the second insulation porcelain 132.

The lead wires 12 extend to outside of the gas sensor 1 through the lead wire insertion holes 32 formed in the elastic insulation member 3 disposed in the base portion of the air cover 2.

The air cover 2 is made of stainless steel and, as above mentioned, has calking portions 20 which radially calk the elastic insulating member 3 at two axially spaced locations. The calking portions 20 secure the lead wire insertion holes 32 of the elastic insulating member 3 fast to the lead wires 12.

As shown in FIGS. 1-3 and FIGS. 6-8, in this example embodiment, the elastic insulating member 3 is comprised of two members 3a, 3b which are axially stacked, the two passage portions 31 are formed between the two members 3a, 3b. Namely, as shown in FIGS. 7-8, grooves 31a, 31b, having semicircle cross-section shapes, are formed two members 3a, 3b. The passage portions 31 are formed by combining the grooves 31a, 31b with each other.

As shown in FIGS. 2-8, the elastic insulating member 3 has an outer air path groove 313 continuously formed on the entire outer circumference thereof and an outer openings 312 of the passage portions 31 are disposed in the outer air path groove 311. Furthermore, as shown in FIGS. 2 and 4-7, the elastic insulating member 3 has an inner air path groove 314 continuously formed on an entire inner circumference of the longitudinal hole 30 thereof and inner openings 313 of the passage portions 31 are disposed on the inner air path groove 314.

As shown in FIGS. 2, 3, 6, and 7, the base portion of the tubular member 4 is formed as a head portion 40 whose outer diameter is larger than other portions thereof. The head portion 40 directly contacts with the end portion 501 of the air permeability filter 5.

Since the end portion 501 of the air permeability filter is not waterproof, adapting the above structure prevent water from penetrating into the gas sensor 1 through the end portion 501 of the air permeability filter 5.

Figure 4:
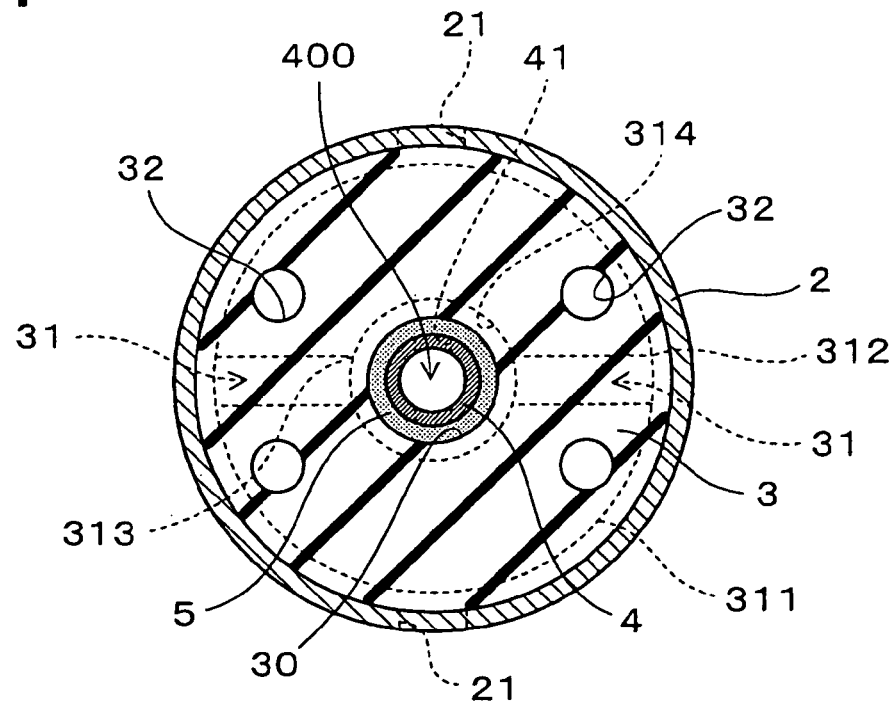
FIG. 4 is a cross-sectional view of the base portion of the gas sensor taken along line IV-IV of FIG. 2.
Figure 5:
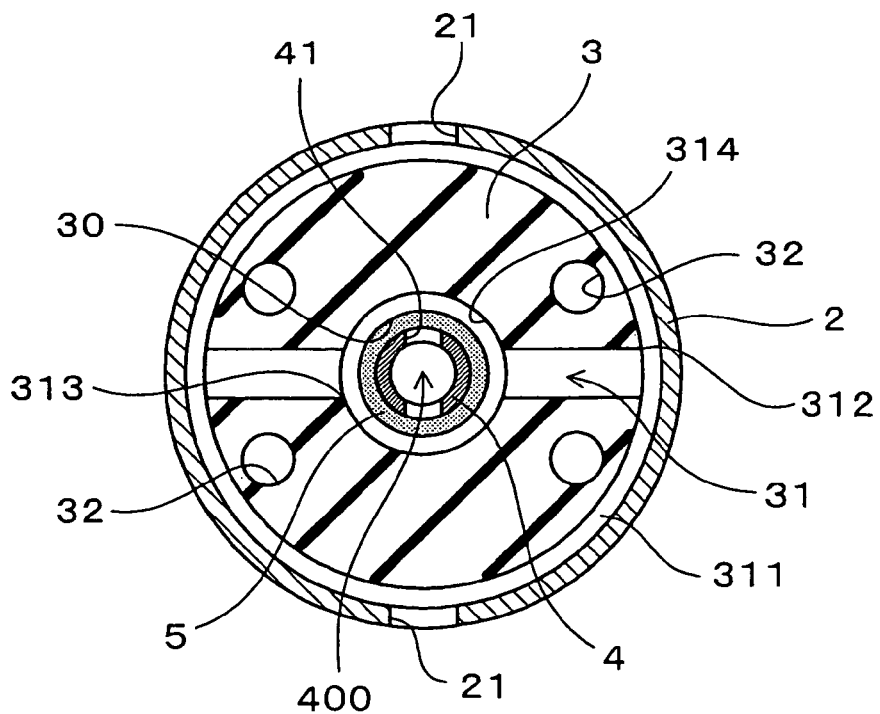
FIG. 5 is a cross-sectional view of the base portion of the gas sensor taken along line V-V of FIG. 2.
Figure 6:
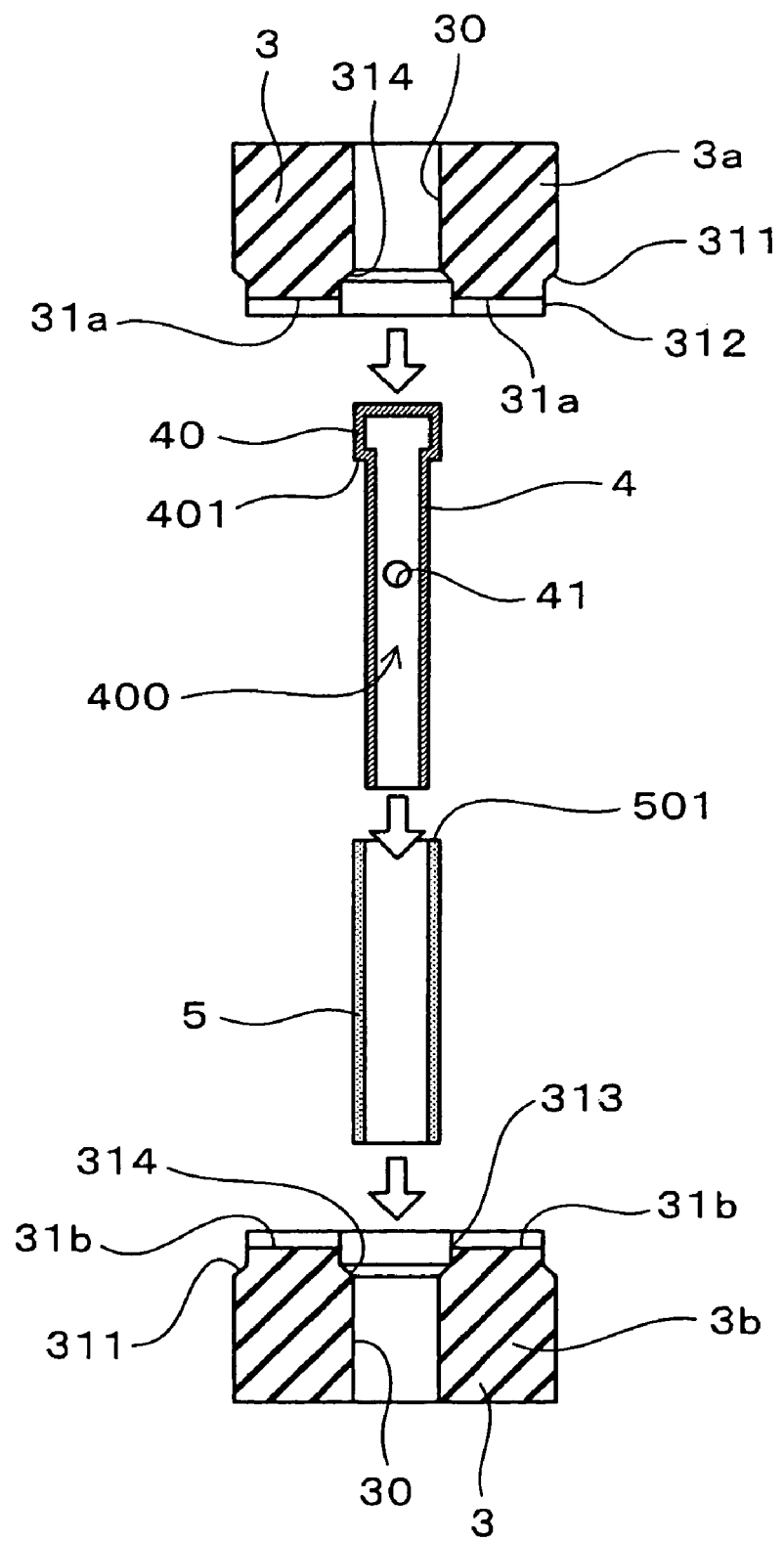
FIG. 6 is a longitudinal sectional view which shows installation of the elastic insulating member, the tubular member, and the air permeability filter of the gas sensor according to the first example embodiment of the present invention.

Furthermore, as shown in FIGS. 4 and 5, the air vent 21, the passage portion 31 and the through hole 41 are not disposed in line. More specifically, in this example, the elastic insulating member 3 is disposed inside of air cover 2 so that the axis of the passage portion 31 is off set from the direction of air vent 21 by 90°.

Even though the air vent 21 of the air cover 2 does not face the outer opening 312 of the passage portion 31 in line, the air from the air vent 21 can be easily introduced to the outer opening 312 of the passage portion 31 through the outer air path groove 311.

On the other hand, the tubular member 4 is inserted into the longitudinal hole 30 so that the direction of the through hole 41 is off set from the axis of the passage portion 31 by substantially 90°.

Even though the inner opening 313 of the passage portion 31 does not face the through hole 41 of the tubular member 4 in line, the air from the passage portion 31 can be easily introduced to the through hole 41 through the inner air path groove 314 and the air permeability filter 5.

An advantage of off setting, the air vent 21, the passage portion 31 and the through hole 41 is that foreign objects can not easily reach the air permeability filter 5 on the through hole 41, so that clogging can be reduced.

Next, the introduced air path of the gas sensor 1 in this example will be described.

The introduced air from the air vent 21 of the air cover 2 is introduced to the outer air path groove 311 formed on the outside face of the elastic insulating member 3. This air is then introduced through the outer opening 312 to the passage portion 31. Then, the air is introduced from the inner opening 313 to the inner air path groove 314. Next, the air from the inner air path groove 314 is introduced through air permeability filter 5 and through the through hole 41 to the inner space 400 of the tubular member 4.

Since the tubular member 4 has an opening at the top end side, the air introduced from the inner space 400 of the tubular member 4, is introduced to the reference gas space formed in the sensor element 10.

The effects and operation according to the above-described embodiment will now be described.

As shown in FIGS. 1-5, the air permeability filter 5 is retained by being crimped between the elastic insulating member 3 and the tubular member 4. Therefore, when the gas sensor 1 is used, even if the permeability filter 5 is deteriorated from heat exposure, such as contracting, the close adhesion property between the permeability filter 5 and the elastic insulating member 3 can be secure.

More particularly, even if the permeability filter 5 experiences heat deterioration, the elasticity power of the elastic insulating member 3 against the tubular member 4 can maintain the close adhesion at the boundary between the permeability filter 5 and the elastic insulating member 3 by following the changing shape of the permeability filter 5. As a consequence, the air permeability portion of the introducing path for outside air will not lead to a deterioration of the water proof property of the assembly. Therefore, the heat deterioration of the permeability filter 5 is compensated by the elasticity of the elastic insulating member 3.

Furthermore, as shown in FIGS. 1-7, the air permeability filter 5 is held in the longitudinal hole 30 of the elastic insulating member 3, whose coefficient of thermal conductivity is small. Therefore, the heat existing outside of the gas sensor 1 cannot be easily conducted from the air cover to the air permeability filter 5, so that heat deterioration of the air permeability filter 5 itself can be avoided in the first place.

As shown in FIGS. 1-3 and as method above, the air cover 2 has calking portions 20 at multiple axially spaced positions and the air vent 21 is formed between the multiple calking portions. Therefore, the air can be easily introduced from the air vent 21 and, the infiltration of the water from a clearance between the air cover 2 and the elastic insulating member 3 can be prevented.

Furthermore, the gas sensor 1 retains the lead wires 12 at least at two position along the axis of the elastic insulating member 3. Therefore, fluctuations of the lead wires 12 out side of the gas sensor 1 cannot easily transmit into the gas sensor 1, as a result, the lead wires 12 are prevented from breaking inside of the gas sensor 1. Also, since the calking portions 20 are at several positions, a bending stress of the lead wire 12 inside of the calking portion 20 due to fluctuation of the lead wire 12 can be reduced.

As shown in FIGS. 1-3 and 6-8, since the elastic insulating member 3 is comprised of two members 3a, 3b that are axially stacked, and because the two passage portions 31 are defined between the two members 3a and 3b, the elastic insulating member 3 can be easily formed without difficult manufacture processes.

As the above described, this example embodiment provides an improved structure for the gas sensor that prevents deterioration of the waterproof properties of the permeability filter due to heat deterioration of the filter.

Although in the above-described example, the elastic insulating member 3 is formed from two members 3a, 3b. The elastic insulating member 3 may be made as a uniform member. In such a case, since the number of the components of the gas sensor 1 is decreased, the number of manufacture processes can be reduced. In such a case, the passage portion 31 can be made by a hole drilling.

The gas sensor provided according to this example embodiment can be a NOx sensor, an oxygen sensor, an air-fuel sensor and so on.

EXAMPLE 2

Figure 9:
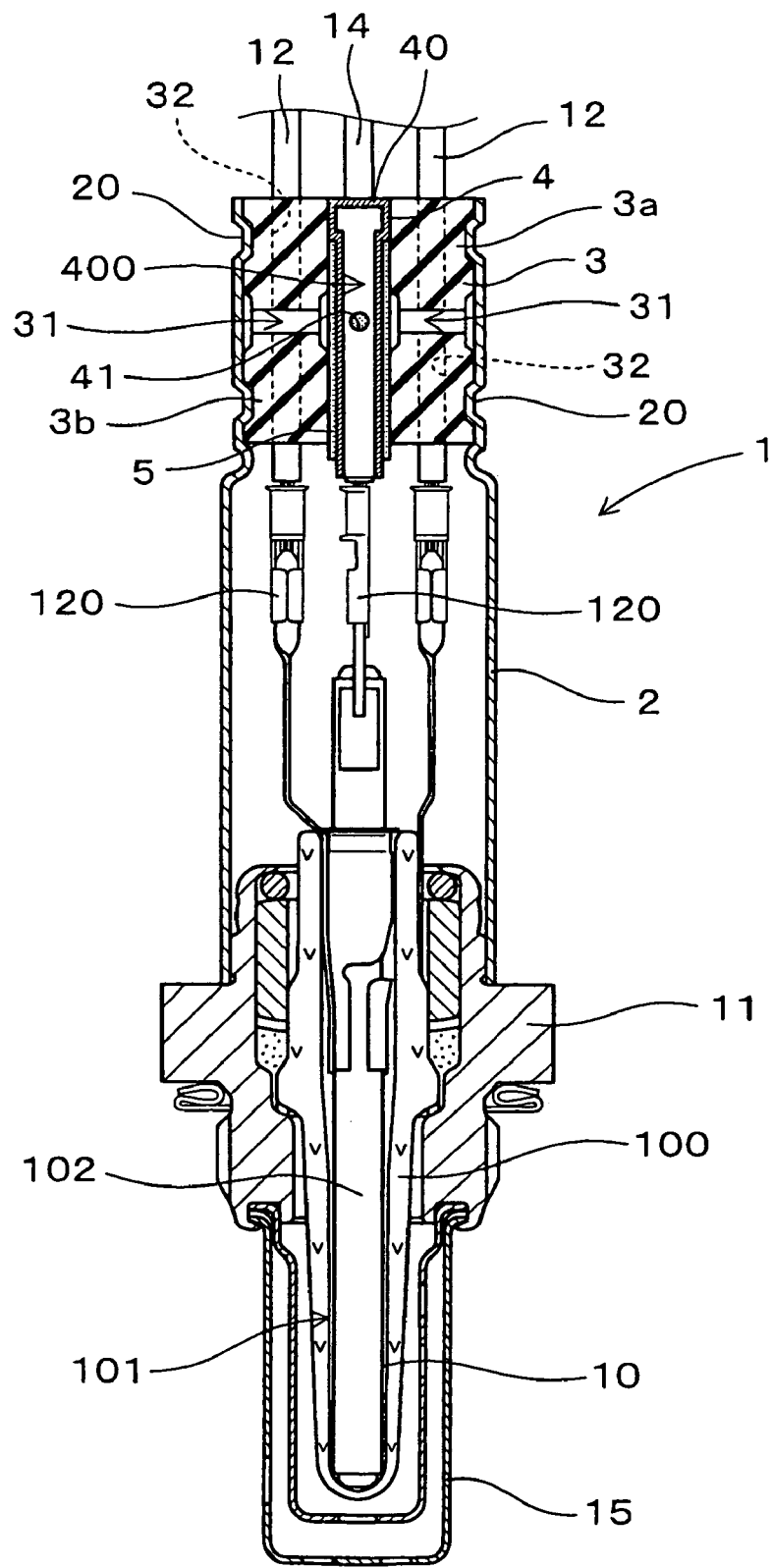
FIG. 9 is a longitudinal sectional view which shows a gas sensor according to a second example embodiment of the present invention.

As shown in FIG. 9, this example has a gas sensor 1 that has a hollow-shaped sensor element 10 having a closed end portion. More particularly, sensor element 10 has a hollow-shaped electrolyte body 100, electrode layers (not shown) disposed as a pair on the inner surface and outer surface of the electrolyte body 100. Furthermore, an atmospheric gas chamber 101 is formed in the electrolyte body 100, and a heater 102 having a heater portion is disposed in the atmospheric gas chamber 101. At the end of both of the sensor element 10, terminal 120 are provided to connected the heater 102 and the electrode pair with lead wires 12 and 14.

Otherwise the composition, the function and the effect are same as in example 1.

EXAMPLE 3

Figure 10:
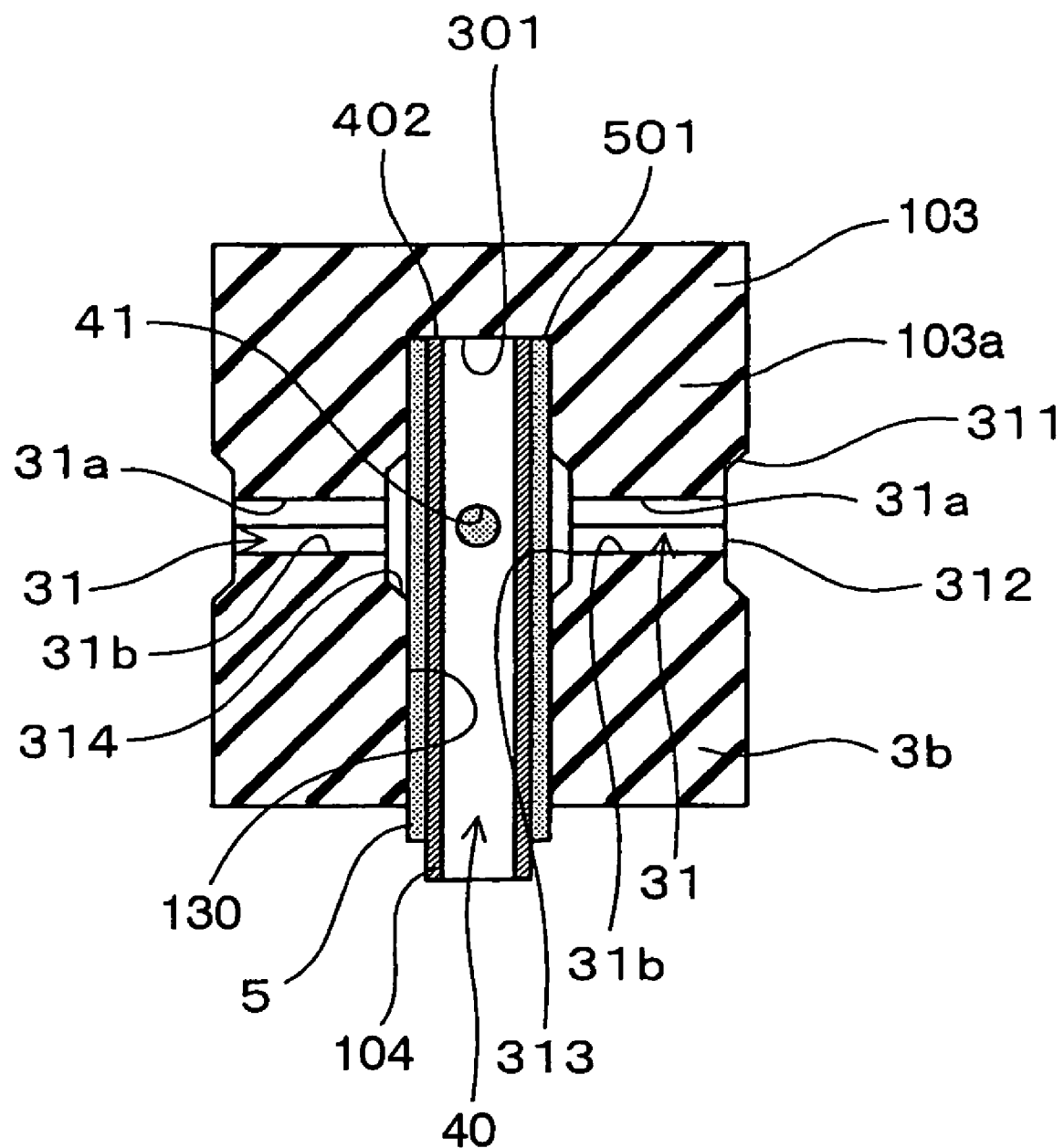
FIG. 10 is a longitudinal sectional view which shows the elastic insulating member, the tubular member, and the air permeability filter of a gas sensor according to a third example embodiment of the present invention.

In this Example, as shown in FIG. 10, the longitudinal bore 130 of the elastic insulating member 103 is not have a through-hole, since it is closed at the base end thereof in member 103a. Also, the tubular member 104 of this example does not have head portion (element 40 in FIG. 6). Thus, both the base portion 402 of the tubular member 104 and the end portion 501 of the base side of the air permeability filter 5 directly touch the base end face 301 inner of the longitudinal bore 130.

Furthermore, an inner chamber 410 of the tubular member 104 is opened at both the base side and the top side.

The composition of this example embodiment is otherwise the same as in Example 1

In this example, since the longitudinal bore 130 is closed at the base side thereof, even though the base side of the tubular member 4 is opened, water does not penetrate at either the tubular member 104 or the end portion 501 of the air permeability filter 5.

The function and the effect of this example embodiment are otherwise the same as in Example 1.

EXAMPLE 4

In this example, as shown in FIGS. 11-14, the multiple members 203a, 203b comprising the elastic insulating member 203 directly touched at multiple foot portions 33 which protrude from the member 203a.

Figure 12:
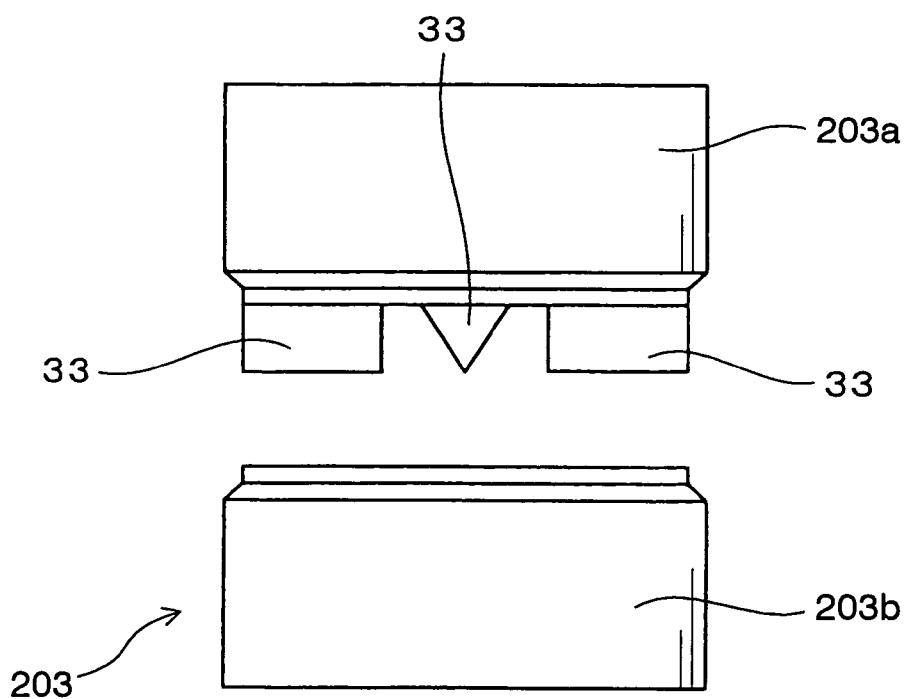
FIG. 12 is an exploded elevational view which shows the two members of the elastic insulating member of gas sensor according to the forth example embodiment of the present invention.
Figure 14:
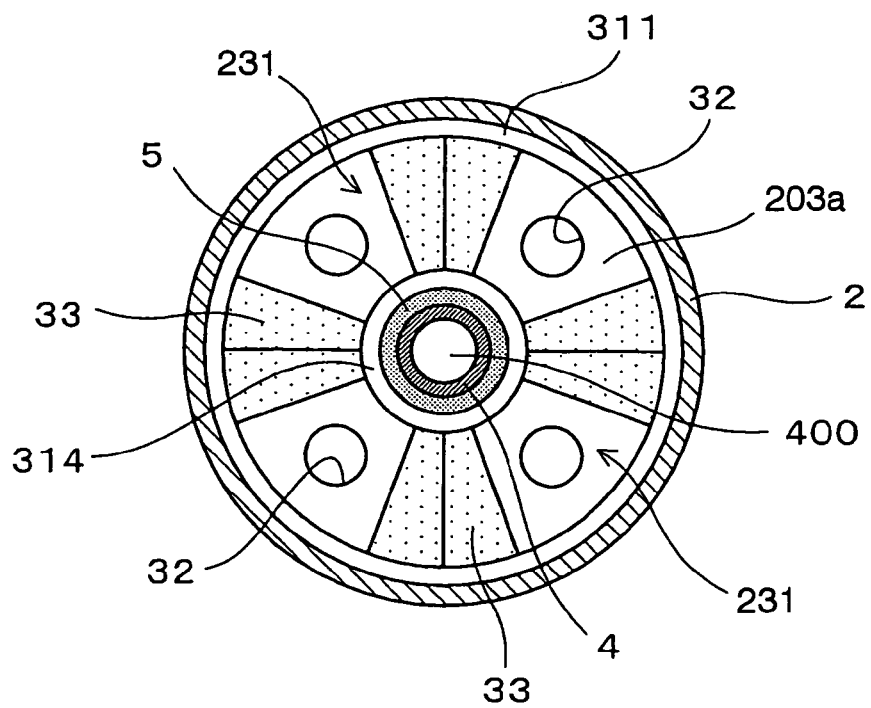
FIG. 14 is a radial cross-sectional view taken along line XIV-XIV of FIG. 13.

More particularly, as shown in FIGS. 12 and 14, the member 203a disposed at the base side defines four-foot portions 33 on the top side surface thereof. The foot portion 33 has the shape that tapers in an axial direction toward to the top end side. Thus the foot portion 33 has a substantially triangular shape in the radial direction of the gas sensor 1. Furthermore, the foot portions have a wedge shape in axial section, as seen in FIG. 14.

Figure 11:
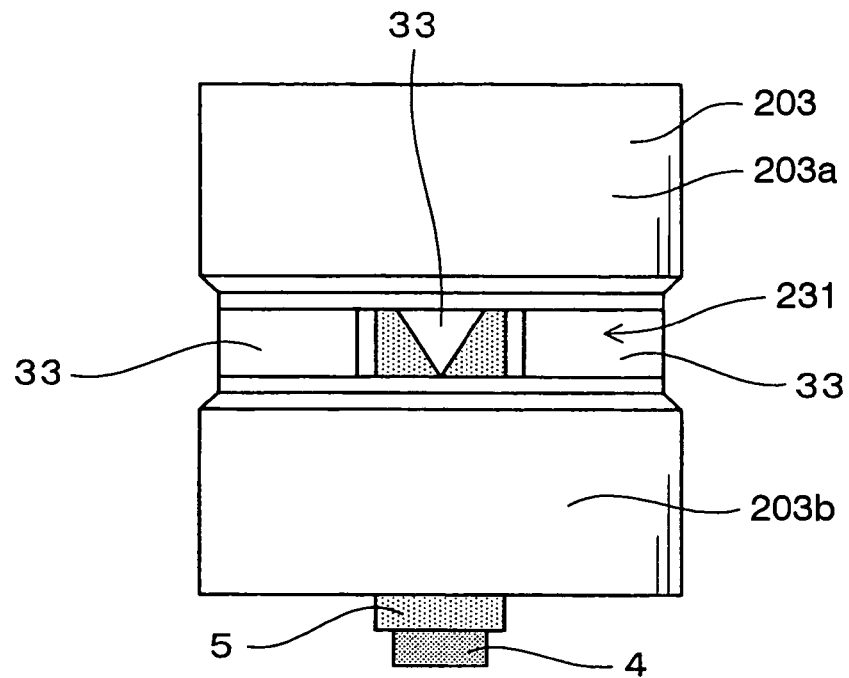
FIG. 11 is a longitudinal sectional view which shows the elastic insulating member, the tubular member, and the air permeability filter of a gas sensor according to a forth example embodiment of the present invention.
Figure 13:
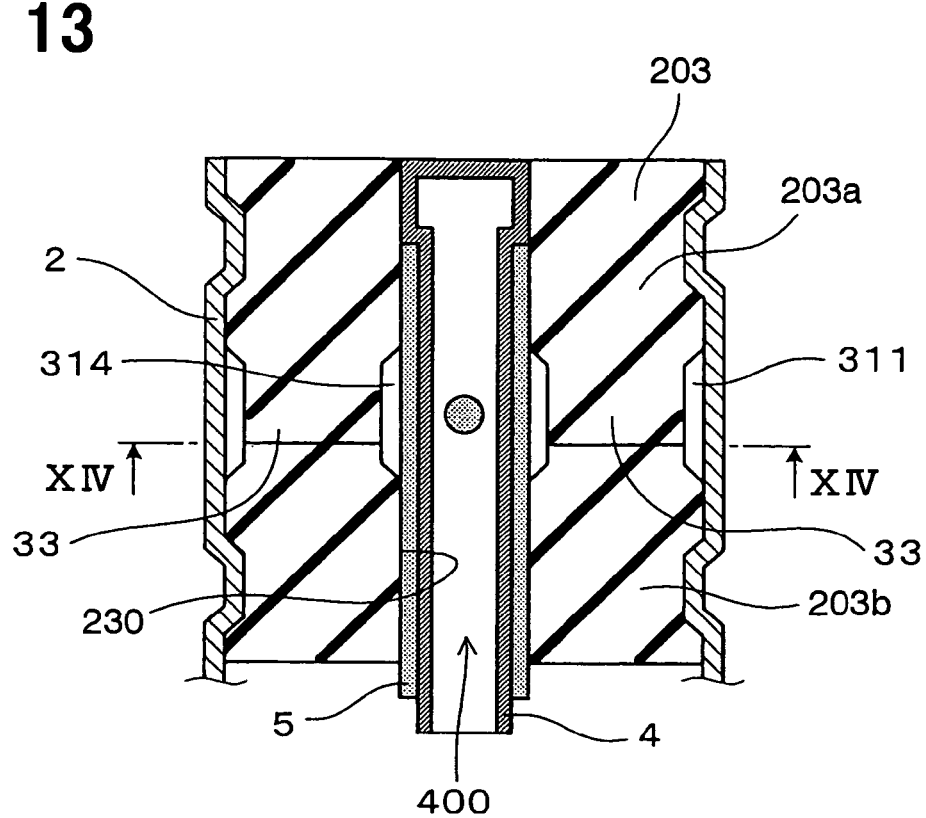
FIG. 13 is a longitudinal sectional view which shows the elastic insulating member, the tubular member, and the air permeability of the gas sensor according to the forth example embodiment of the present invention.

As shown in FIGS. 11 and 13, the tubular member 4 and the air permeability filter 5 are inserted into the longitudinal bore 230 of the members 203a, 203b and then tubular members 203a, 203b are assembled so that the foot portions 33 of the member 203a directly touch with the end base side surface of the member 203b. The passage portions 231 are formed between the foot portions 33 in the space formed between members 203a, 203b.

In this example, the multiple members 203a, 203b can directly touch while keeping the contact area small. Therefore, even though multiple member 203a, 203b thermally expand, the multiple members 203a, 203b can avoid slipping against the air permeability filter 5 or the air cover 2 by reducing the pushing power against each other. Consequently, the gas sensor 1 can have an improved waterproof property.

The other aspects of this example embodiment are the same as in Example 1.

The shape and the numerous of the foot portion 33 is not limited according to the illustrated example. Indeed, the number and shape of the foot portions can be varied. Furthermore, the foot portions 33 can protrude from the base end side surface of members 203b, or from both of the members 203a, 203b.

EXAMPLE 5

Figure 15:
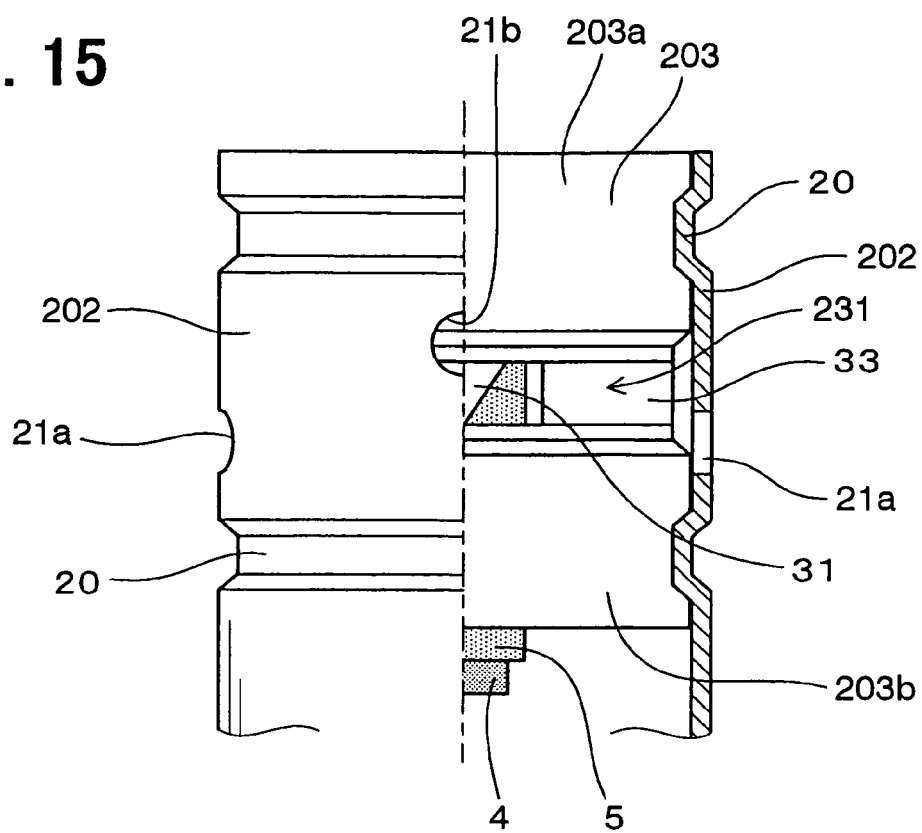
FIG. 15 is a partial longitudinal sectional view which shows a base portion of a gas sensor according to a fifth example embodiment of the present invention.

In this example, as shown in FIG. 15, the multiple air vents 21 are disposed in different positions in the axial direction of the gas sensor 1.

More particularly, the four vents 21 are not equally spaced between two calking portions 20 of the air cover 2. Instead, two of the diametrically opposed air vents 21a are formed at the top end side of the air cover 202 and the other two air vents 21b are formed at the base end side of the air cover.

Therefore, adjacent air vents 21a, 21b are disposed in a different axial position to define a zigzag pattern.

In this example, even though the elastic insulating member 203 is axially fixed against the air cover 202, the water introduced from the air vents 21a, 21b to the passage portions 231 can be efficiently exhausted through the air vents 21a, 22b. Thus, the air permeability filter 5 is prevented from getting soaked will water collected in the passage portions 231. Furthermore, clogging of the air permeability filter 5 can be efficiently avoided.

The other aspects of this example embodiment are the same as in Example 4.

EXAMPLE 6

Figure 16:
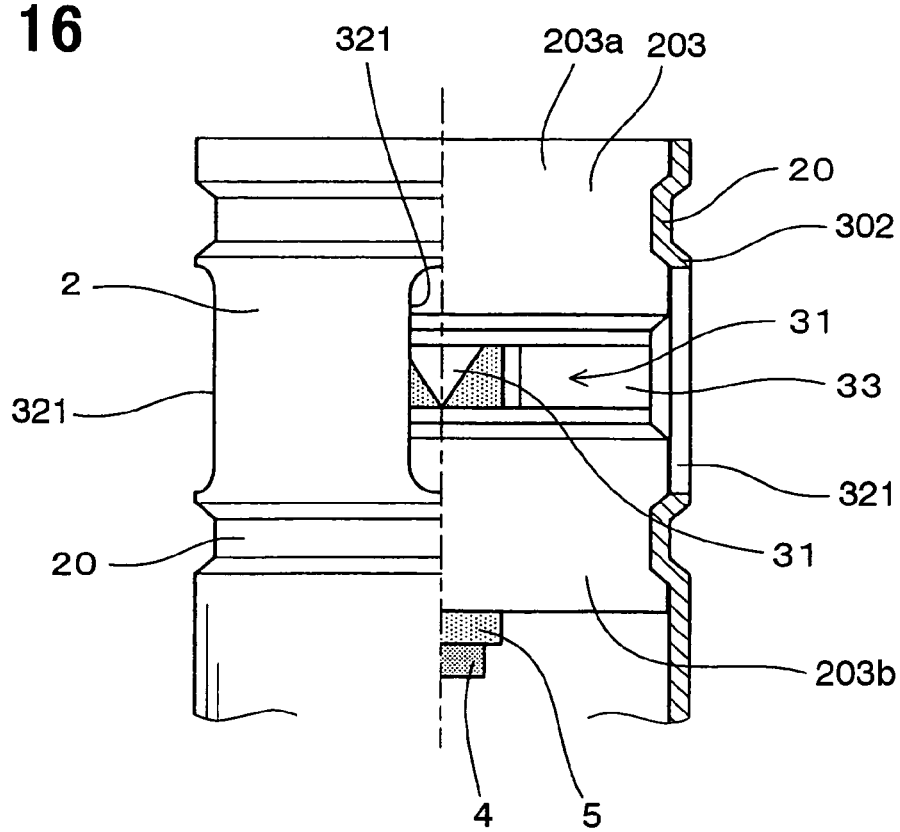
FIG. 16 is a partial longitudinal sectional view which shows a base portion of a gas sensor according to a sixth example embodiment of the present invention.

In this example, as shown in FIG. 16, the shape of the air vent 321 is an oval shape having a long axis extending in axial direction of the gas sensor 1. The length of the long axis of the air vent 321 is longer than that of the passage portion 31.

The base position of the air vent 321 is nearer the base side than that of the passage portion 31, and the top portion of the air vent 321 is nearer the top side than that of the passage portion 31.

In this example, passage water introduced from the air vents 321 to the passage portions 31 can be efficiently exhausted through a part of the air vent 321. Furthermore, air can be introduced from the air vent 321 to the passage portions 31. In this way, the air permeability filter 5 is prevented from getting soaked with water that collects in the passage portions 31, and clogging of the air permeability filter 5 can be efficiently avoided.

Since the shape of the air vent 21 is an oval shape, foreign material having a large diameter can be prevented from entering the gas sensor 1.

The other aspects of this example embodiment are the same as in the Example 4.

COMPARATIVE EXAMPLE 1

Figure 17:
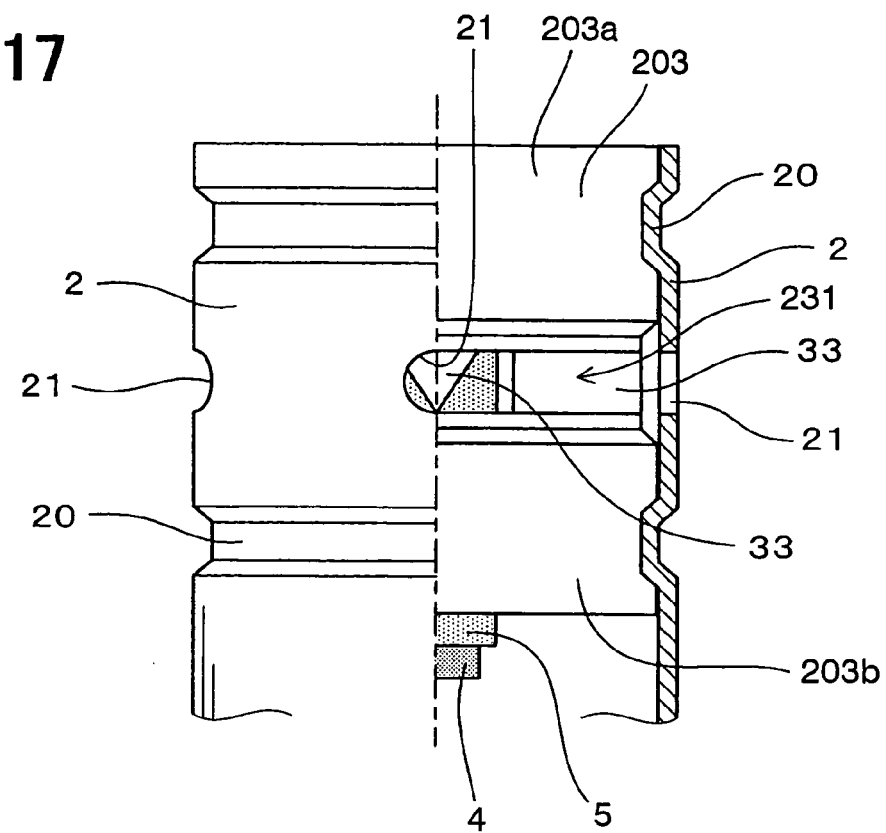
FIG. 17 is a partial longitudinal sectional view which shows a base portion of a gas sensor according to a first comparative example.
Figure 18:
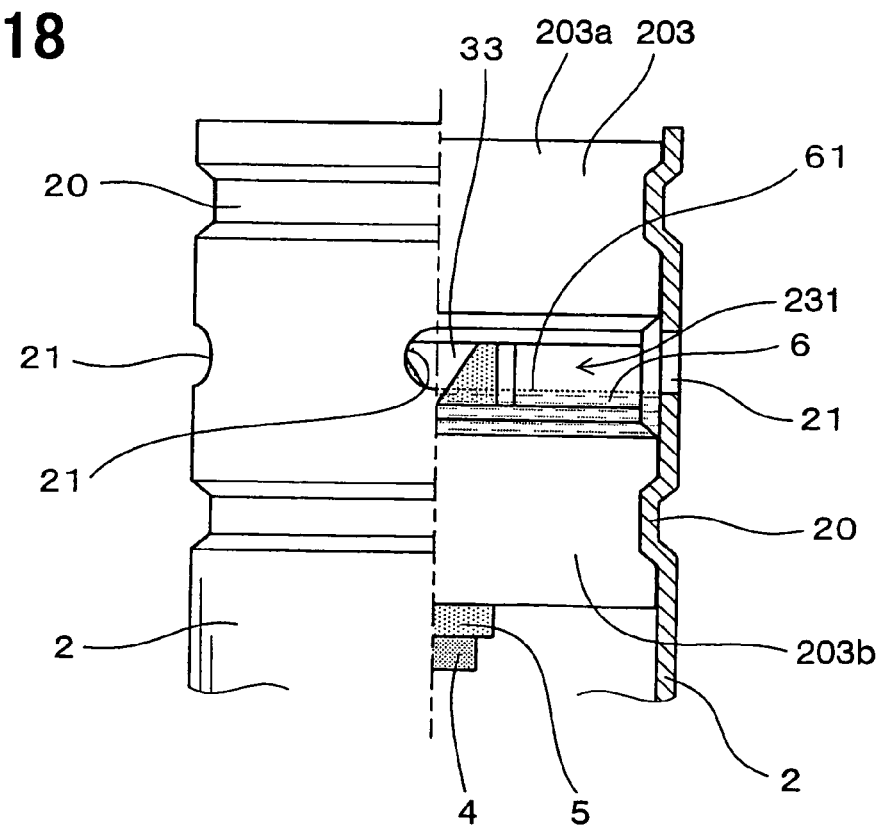
FIG. 18 is another partial longitudinal sectional view which show the base portion of the gas sensor according to the first comparative example.

In this Example, as shown in FIG. 17, the multiple air vents 21 are disposed at the same axial position and centered with the passage portions. In FIG. 18, the elastic insulating member 203 is fixed in an axially off set position against the air cover 2.

According in the gas sensor 1 of Example 4, FIG. 17 shows the elastic insulating member 203 is disposed at an accurate position, namely, the center of the air vent 21 is the same as the center of the passage portion 231. Furthermore, according in the gas sensor 1 of showing in the Example 4, FIG. 18 is showing that the elastic insulating member 203 is disposed at a slip position, namely, the center of the air vent 21 is different from that of the passage portion 231.

When the elastic insulating member 3 is disposed on the accurate position, as shown in FIG. 17, even though water penetrate through the air vent 21, the gas sensor 1 can prevent water from collecting in the passage portion 31. Thus, collection of water in the passage portion can be avoided, since the surface level of the water is always at the more top end side than the base end side of the air vent 21.

As shown in FIG. 18, however, when elastic insulating member 203 is fixed after having slipped to the top end side, the top end side of the passage portion 31 is disposed at a lower position than the top end side of the air vent 21. Thus, water 6 introduced from the air vent 21 is collected in the passage portion 31.

Since the air permeability filter 5 will soak in the water 6 collected in the continuous portion 31, the air permeability filter 5 may become clogging.

In the result, it is difficult for the gas sensor 1 to get accurately detect the concentration of the particular gas.

In the extreme case where the top end side of the air vent 21 is located more to the base end side than the top end side of the passage portion 231, the water may fill the passage portion 231 and thus completely close the introducing air path.

On the other hand, when the gas sensor 1 of the Example 5 (as shown in FIG. 15) or that of the Example 6 (as shown in FIG. 16) are adopted, even if the elastic insulating member 3 is slightly slipped in the axial direction of the gas sensor 1 with respect to air cover 2, water can be easily exhausted through a part of the air vents 21a, 21b, 321. Accordingly, water is prevented from collecting in the passage portion 31 and the air permeability filter 5 is prevented from clogging.

COMPARATIVE EXAMPLE 2

Figure 19:
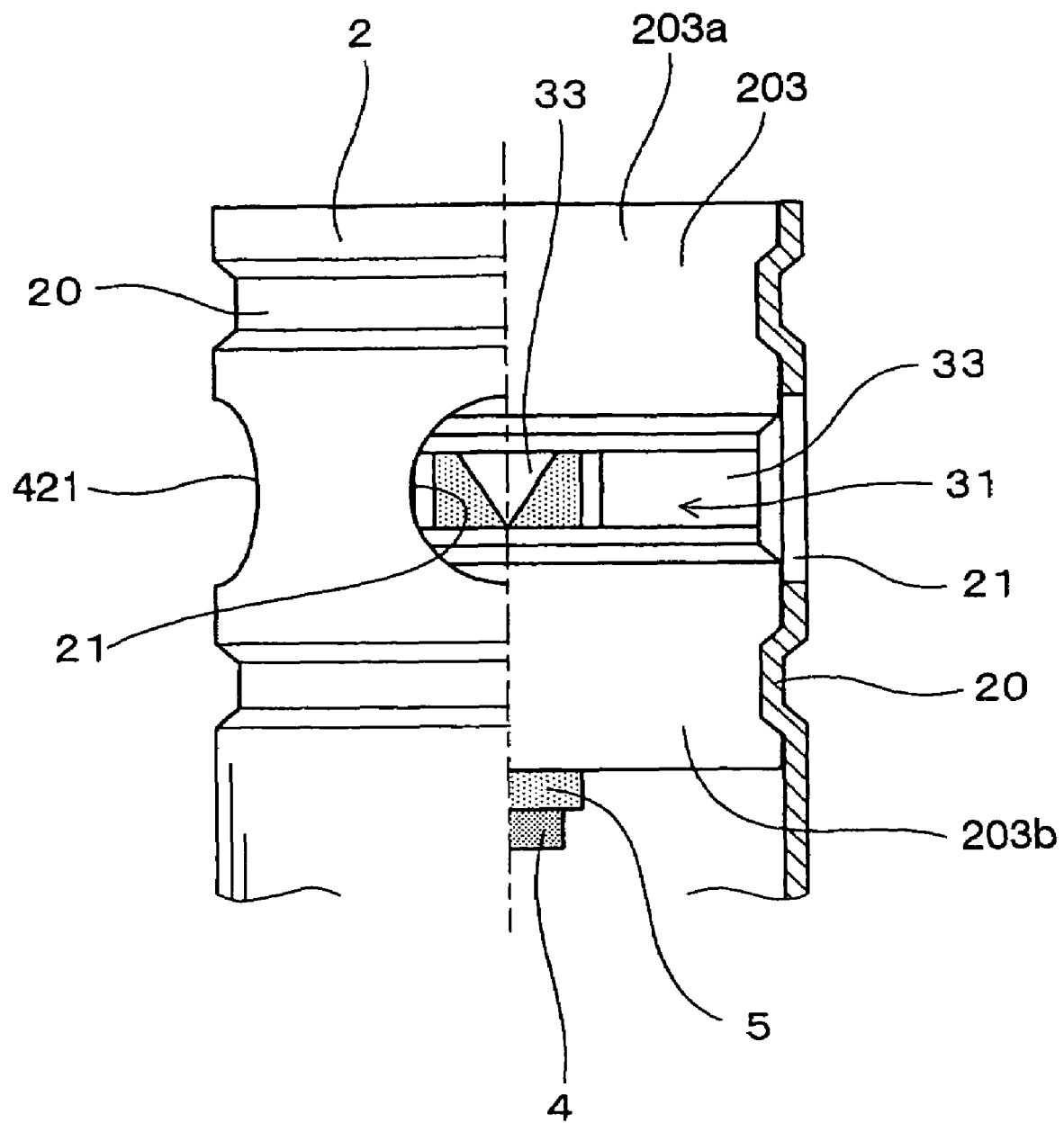
FIG. 19 is a partial longitudinal sectional view which shows a base portion of a gas sensor according to a second comparative example.
Figure 20:
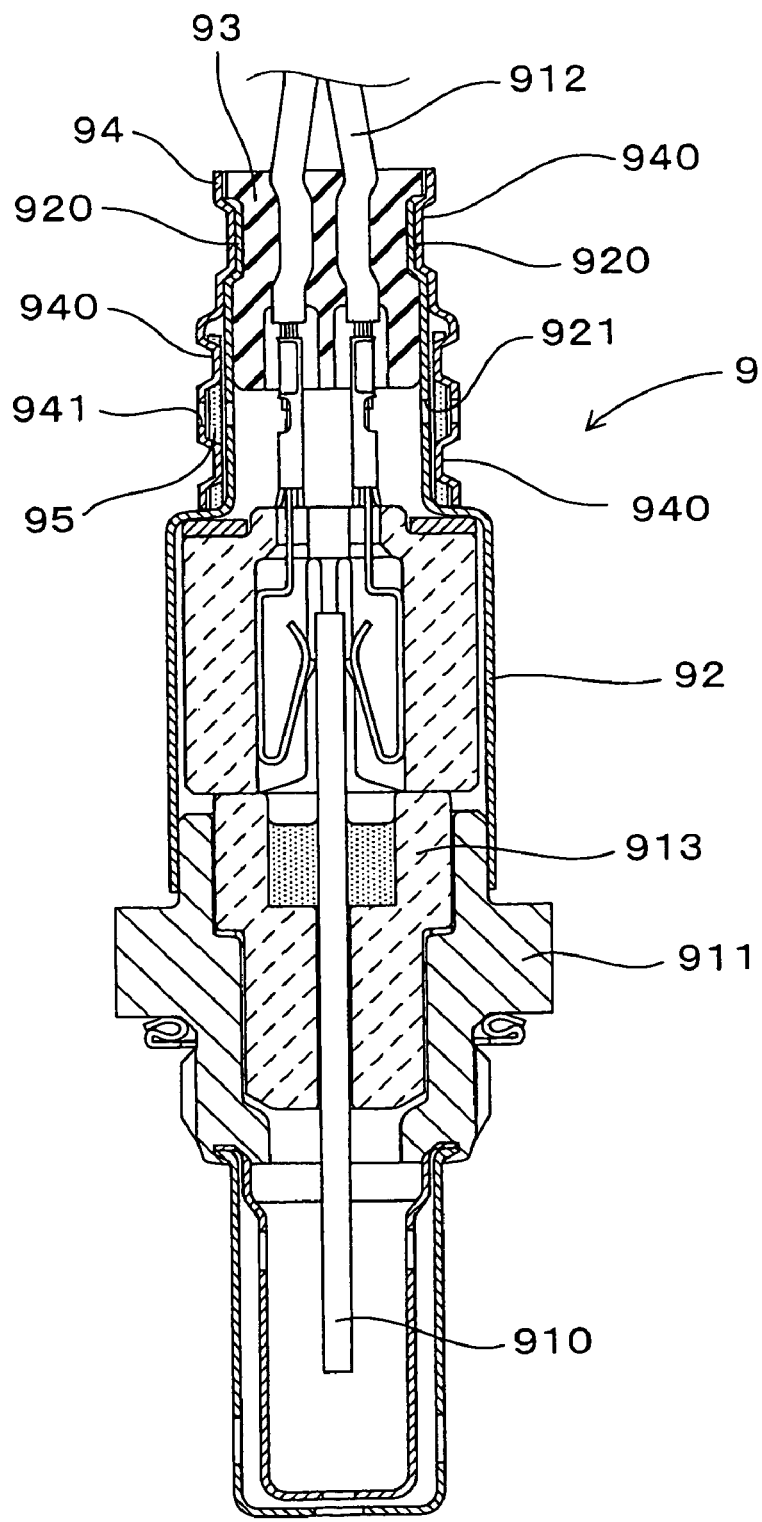
FIG. 20 is a longitudinal sectional view which shows a gas sensor according to the prior art.

In this example, as shown in FIG. 19, the air vent 421 has the shape of a large circle whose diameter is longer than the length of the axis direction of the passage portion 31.

In this case, similar to Example 6, even when the elastic insulating member 203 is located slightly off in the axial direction of the gas sensor, water is prevent from collecting in the passage portion 31. However big foreign materials can enter into the gas sensor 1 through the air vent 421 and clogging of the filter may occurred.

On the other hand, in Example 6, since the shape of the air vent 21 is oval, foreign material having a large diameter can be blocked from entering into the gas sensor 1.

Although the present invention has been fully described in connection with the preferred embodiments thereof with reference to the accompanying drawings, it is to be noted that various changes and modifications will become apparent to those skilled in the art.

What is claimed is:

1. A gas sensor comprising:
    a sensor element for detecting the concentration of a particular gas contained in a measurement gas;
    a housing holding said sensor element;
    an air cover installed on an end of said housing;
    a lead wire making an electric contact with said sensor element;
    an elastic insulating member having a lead wire insertion hole for receiving said lead wire and sealing a base portion of said air cover, wherein said elastic insulating member has a longitudinal hole, formed in the axial direction thereof and open at an end thereof, and a passage portion communicating between said longitudinal hole and an outer side thereof;
    a tubular member forming an internal space that is open at an end thereof and having a through-hole penetrating between said internal space and an outer side of said tubular member, wherein the tubular member is disposed in said longitudinal hole;
    an air permeability filter wound around an outer circumference of said tubular member and crimped between said elastic insulating member and said tubular member, wherein said air cover is radially calked at plural axially spaced calking portions to retain said elastic insulating member; and
    an air vent, through which air is admitted into said passage portion of said elastic insulating member, the air vent being disposed between said multiple calking portions.

2. A gas sensor according to claim 1, wherein said passage is a radial bore in said elastic insulating member which is made as a uniform member.

3. A gas sensor according to claim 1, wherein an outer air path groove is continuously formed on an entire outer circumference of said elastic insulating member, an outer opening of said passage portion being disposed on said outer air path groove.

4. A gas sensor according to claim 1, wherein an inner air path groove is continuously formed on an entire inner circumference of said elastic insulating member, an inner opening of said passage portion being disposed on said inner air path groove.

5. A gas sensor according to claim 1, wherein said air vent, said passage portion, and said through hole are not linearly aligned.

6. A gas sensor according to claim 1, wherein said air permeability filter is made of porous PTFE.

7. A gas sensor according to claim 1,
    wherein shape of said air vent is oval, having a long axis parallel to the axis of said gas sensor, and
    the length of the long axis of said air vent is longer than the axial height length of said passage portion.

8. A gas sensor according to claim 1, wherein said air cover is made of metal material.

9. A gas sensor according to claim 1, wherein the number of said air vents corresponds with the number of said passage portions.

10. A gas sensor according to claim 1, wherein multiple air vents are disposed about the circumference of said air cover in various axial positions.

11. The sensor according to claim 10, wherein one of the multiple air vents is diametrically opposed to another of the multiple air vents.

12. A gas sensor according to claim 10,
    wherein at least one of said air vents is formed at the top end side of said air cover with respect to said passage portion, and
    at least one of the other air vents is formed at the base end side of said air cover with respect to said passage portion.

13. The sensor according to claim 12, wherein the at least one of the multiple air vents is diametrically opposed to the at least one of the other air vents.

14. A gas sensor according to claim 1, wherein said air permeability filter is disposed so as to avoid exposure of the end portion thereof to atmosphere.

15. A gas sensor according to claim 14,
    wherein a base portion of said tubular member is formed as a head portion whose outer diameter is larger than other portions of said tubular member, and
    said end portion of said air permeability filter is directly contacted with said head portion so as to avoid exposure to atmosphere.

16. A gas sensor according to claim 14,
    wherein a longitudinal bore of said elastic insulating member is closed at a base end of said tubular member, and
    said end portion of said air permeability filter directly touch said base end face inner of said longitudinal bore so as to avoid exposure to atmosphere.

17. A gas sensor according to claim 1, wherein said elastic insulating member is comprised multiple members that are axially stacked.

18. A gas sensor according to claim 17, wherein said passage portion is formed between said multiple members.

19. A gas sensor according to claim 17, wherein said multiple members comprising said elastic insulating member directly contact via multiple foot portions which protrude from at least one of said multiple members.

20. A gas sensor according to claim 19, wherein said foot portions have shape that tapers in an axial direction toward to the top end side.

* * * * *